United States Patent [19]
Stönner

[11] Patent Number: 4,482,766
[45] Date of Patent: Nov. 13, 1984

[54] PRODUCTION OF FATTY ALCOHOL WITH RECOVERY THEREOF FROM THE HYDROGENATION CATALYST

[75] Inventor: Hans-Martin Stönner, Schwalbach, Fed. Rep. of Germany

[73] Assignee: Metallgesellschaft Aktiengesellschaft, Frankfurt am Main, Fed. Rep. of Germany

[21] Appl. No.: 497,328

[22] Filed: May 23, 1983

[30] Foreign Application Priority Data

Jun. 5, 1982 [DE] Fed. Rep. of Germany ....... 3221307

[51] Int. Cl.[3] ..................... C07C 29/136; C07C 29/76

[52] U.S. Cl. ....................................... 568/885; 502/22; 502/318; 568/913

[58] Field of Search ......................................... 568/885

[56] References Cited

U.S. PATENT DOCUMENTS

| | | | |
|---|---|---|---|
| 2,597,074 | 5/1952 | De Bartholomaeis et al. | 568/885 |
| 2,750,429 | 6/1956 | De Nora et al. | 568/885 |
| 3,173,959 | 3/1965 | Rittmeister | 568/885 |
| 3,180,898 | 4/1965 | Eisenlohr et al. | 568/885 |
| 4,259,536 | 3/1981 | Voeste et al. | 568/885 |

*Primary Examiner*—J. E. Evans
*Attorney, Agent, or Firm*—Sprung, Horn, Kramer & Woods

[57] ABSTRACT

In a process of recovering and cleaning catalysts in the continuous production of fat alcohols by a catalytic hydrogenation of fatty acids or fatty acid derivatives at temperatures of 240° to 330° C. and pressures of 200 to 700 bar in the presence of copper-chromium oxide catalysts, wherein the reaction is carried out in the presence of material which has been already reacted, the resulting dispersion is circulated through the filter which is due for cleaning until the contents of the stirring vessel is free of solids and the filter cake is substantially free of product, the liquid from which solids have been removed is separated into cleaning liquor and recovered product by a simple sedimentation in a liquid-liquid separator or by a distillation, the recovered product is fed to the main product, the catalyst which is moistened with the cleaning liquor and substantially free of product is withdrawn and, if required, is dryed.

10 Claims, 2 Drawing Figures

PRODUCTION OF FATTY ALCOHOL WITH RECOVERY THEREOF FROM THE HYDROGENATION CATALYST

BACKGROUND OF INVENTION

Field of Invention

This invention relates to a process of recovering and cleaning catalysts in the continuous production of fatty alcohols by a catalytic hydrogenation of fatty acids or fatty acid derivatives at temperatures of 240° to 330° C. and pressures of 200 to 700 bar in the presence of copper-chromium oxide catalysts, which may be modified by additional components, wherein the feedstock to be hydrogenated is fed to a high-pressure chamber, which communicates with a return pipe, hydrogen and dispersed catalyst are fed to said high-pressure chamber, the contents of the high-pressure chamber are thoroughly mixed, the reaction is carried out in the presence of a large quantity of material which has been entirely or almost completely reacted, surplus hydrogen is withdrawn and recycled to the high-pressure chamber, reaction product and water formed by the reaction are withdrawn, catalyst is circulated through the synthesis reactor, residual catalyst is continuously removed from the end product by means of filters connected in parallel, and spent catalyst is separated by a solid-liquid separation to form a stream which contains fine catalyst particles.

DISCUSSION OF PRIOR ART

In that process and similar processes, the catalyst is thoroughly dispersed by stirring in a corresponding quantity of fatty alcohol product and the resulting dispersion is continuously fed to the reactor cycle. Catalyst at a corresponding rate is continuously withdrawn so that the concentration of catalyst remains substantially constant. Because the feedstock to be hydrogenated is thoroughly mixed with a relatively large quantity of recycled material, which has been partly or completely reacted, the catalyst is handled under mild conditions. The ester formed by the continuous esterification of the fatty acid with the fatty alcohol is neutral and does not deteriorate the catalyst so that the entire process is carried out under very mild conditions but has a high efficiency (German Offenleungschrift No. 28 53 990).

The fatty alcohol product contains catalyst. It is known that the fatty alcohol product can be separated from the catalyst in settling vessels, which are held at 70° C. and have such a size that they permit an average dwell time of 15 hours. In said vessels a major part of the catalyst is continuously removed from the mixture and is withdrawn from the bottom of the vessel as a suspension which contains 20 to 60% catalyst. Last traces of catalyst still contained in the alcohol effluent are removed in a centrifugal clarifier (German No. 11 12 056, U.S. Pat. No. 3,180,898).

It is difficult, however, to remove all alcohol from the catalyst because owing to its large surface area the catalyst firmly retains the alcohol. This fact results in losses of end product. On the other hand it is difficult to regenerate the catalyst although its regeneration is desired for economical reasons. It is particularly difficult to remove from the process, without losses, the increasing amounts of fine catalyst particles which develop as the catalyst is circulated.

It is an object of the invention to avoid these and other disadvantages and to improve and facilitate the recovery and cleaning of the catalyst in the continuous production of fatty alcohols by a catalytic hydrogenation at elevated temperatures and elevated pressure.

SUMMARY OF INVENTION

This object is accomplished in accordance with the invention in that the fine catalyst particles are contacted with heated or cooled cleaning liquor and together with said liquor are stirred in a stirring vessel, and the resulting dispersion is circulated through one of the parallel filters which is due for cleaning until the contents of the stirring vessel are substantially free of solids and the filter cake is substantially free of product, the mixture from which the solids have been removed is separated for a recovery of cleaning liquor and product, the product thus recovered is added to the main product, and the catalyst which is moistened with the cleaning liquor and substantially free of product is dried, if desired, and discharged.

In accordance with a preferred further feature of the invention the cleaning liquor comprises a non-solidifying low-boiling solvent, e.g., of boiling point of 70° to 220° C. at atmospheric pressure, which can be separated by distillation from the washed material.

The cleaning liquor alternatively consists of heated water, e.g., at a temperature of 60° to 90° C., which can be separated by a liquid-liquid separation from the water-insoluble product.

In accordance with a further preferred feature the fine catalyst particles which are still contained in the reaction liquid when the catalyst and part of the reaction product have been removed from said liquid are removed from the reaction chamber, a major part of the catalyst is removed by decanting and/or centrifugation, product is recycled to the reaction chamber, and the phase that contains the fine catalyst particles is transferred to the stirring vessel and admixed to the liquid which is circulated through that filter which is due for cleaning.

The fine catalyst particles which have been removed by decanting and/or centrifugation are desirably admixed to the liquid which is passed through the filter which is due for cleaning.

Within the scope of the invention the moist catalyst is dried in that air or inert gas, which may have been heated, is passed through the catalyst.

In accordance with the invention the cleaning liquor may consist of the reaction water which becomes available during the hydrogenation process, the liquid-liquid separation for removing the reaction water and cleaning liquor from the product is carried out in the same liquid-liquid separator, the water formed by the reaction is withdrawn and is separated into a water-insoluble phase and an aqueous phase by a simple sedimentation in a liquid-liquid separator, the organic phase, after an optional removal of traces of water in a liquid-liquid separator, is added to the main product, and the separated water is fed to the stirring vessel.

The advantages afforded by the invention reside particularly in that a simple and economical process is provided by which the catalyst that has been used in the continuous production of fatty alcohols by a catalytic hydrogenation at elevated temperatures and elevated pressures can be recovered from the reaction material and can be cleaned. Because the fatty alcohol adhering to the catalyst is substantially recovered, the yield of the end product is increased. The catalyst is cleaned to a high purity and can be processed for a recovery of the valuable metals. The process can be used for a recovery in concentrated form of the fine catalyst particles which become available and which otherwise cannot be separated, so that the environment will not be polluted. The apparatus, filters, distilling equipment, liquid-liquid separators and the like which are required for carrying out the invention can easily be operated in a simple manner and require only a low expenditure for monitoring. An additional advantage afforded by a special embodiment of the process resides in that the process can be carried out in such a manner that only a few additional devices are required.

Usually the weight ratio of cleaning liquor, whether it be low-boiling solvent or water, to catalyst fines is 10 to 50.

BRIEF DESCRIPTION OF DRAWINGS

The invention is shown diagrammatically and by way of example in the two drawings annexed hereto, both of which are flow diagrams.

DESCRIPTION OF SPECIFIC EMBODIMENTS

Figure 1:
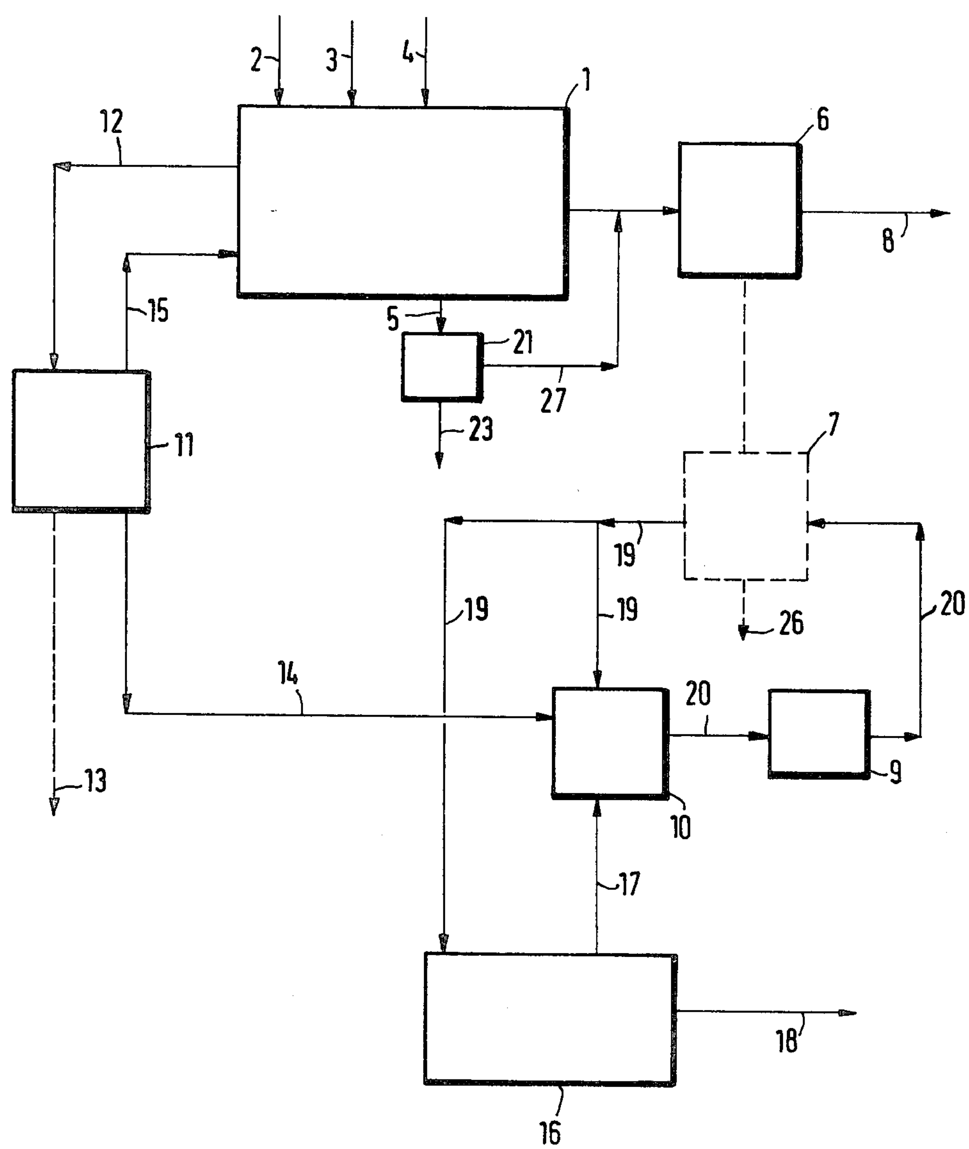

Referring to the drawings,

FIG. 1 illustrates the process according to the invention using an organic or aqueous cleaning liquor.

Figure 2:
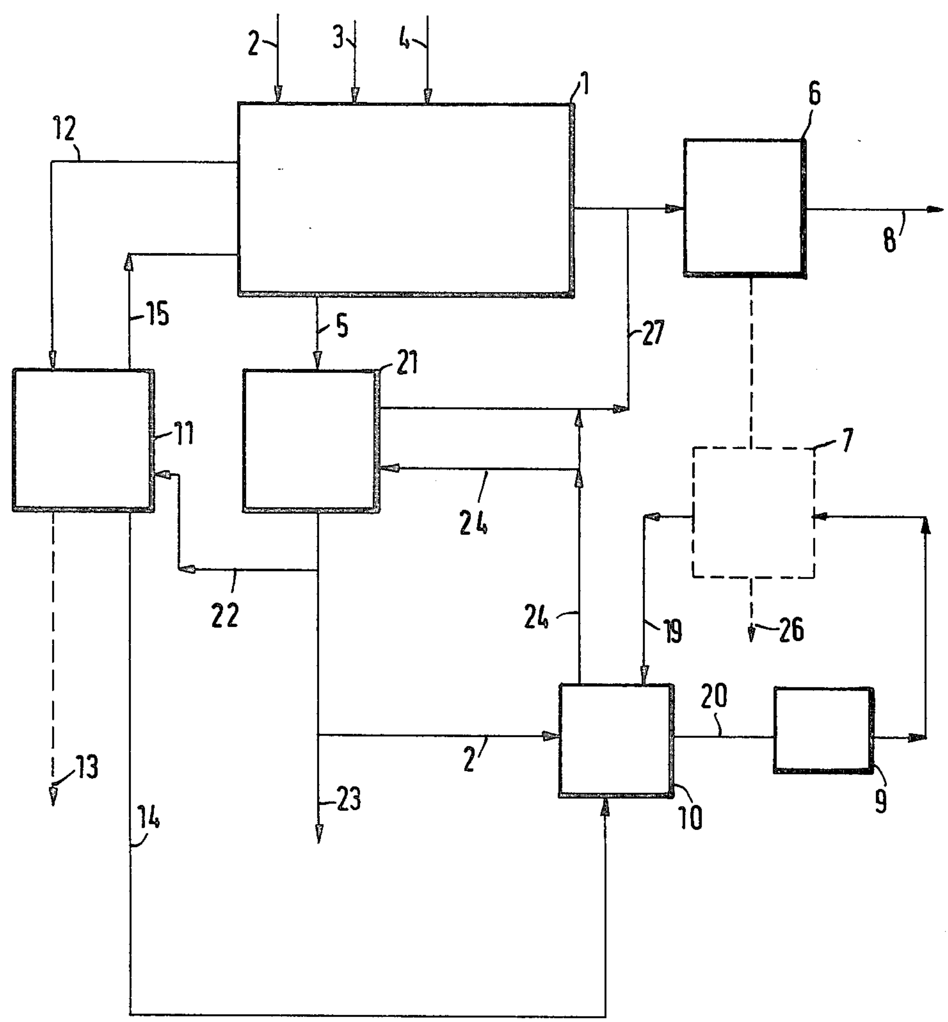

FIG. 2 illustrates the process according to the invention using a cleaning liquor which contains the reaction water that has been withdrawn from the reaction chamber.

The following items are shown in the drawings:

Synthesis apparatus 1; line 2 for feedstock to be hydrogenated; line 3 for feeding hydrogen; line 4 for feeding catalyst; line 5 for withdrawing reaction water; filter 6 in operation; filter 7 which is due for cleaning; line 8 for withdrawing end product; heating and/or cooling device 9; stirring vessel 10; solid-liquid separator (decanter and/or centrifuge) 11; line 12 for withdrawing catalyst dispersion; line 13 for catalyst; line 14 for mixture of fine catalyst particles (1–10 microns) with product or spent catalyst or washing liquor for centrifuge; line 15 for recycling product; separator (liquid-liquid separator or distilling apparatus) 16; line 17 for cleaning liquor; line 18 for recovered product; line 19 for mixture of cleaning liquor and product portions; line 20 for cleaning liquor which contains dispersed catalyst and residual product; liquid-liquid separator 21; line 22 for controlling or rinsing liquid; line 23 for separated reaction water; line 24 for recovered product; line 25 for reaction water used as cleaning liquor; line 26 for withdrawing spent catalyst; line 27 for separated product.

DESCRIPTION OF PROCESS (EXAMPLE)

In accordance with FIG. 1 the feedstock from which fatty alcohol is to be produced by hydrogenation is continuously fed through line 2 to the synthesis reactor 1, which is fed through line 3 with hydrogen and through line 4 with the catalyst comprising copper-chromium oxide, particle size of the catalyst being 1–500 microns. The water formed by the reaction (mixed with reaction product) is continuously withdrawn through line 23. Hydrogenation is effected at a temperature of 300° C. and a pressure of 320 bar above atmospheric pressure. The end product is passed through the filter 6 and then withdrawn through line 8. Fresh catalyst dispersion is continuously fed at a low rate through line 4 into the high-pressure chamber. After 30 passes of the catalyst the filter 6 is due for cleaning.

It is disconnected from the cycle 7 and contacted with cleaning liquor, which has been heated by the heater 9. The mixture of product and cleaning liquor is fed through line 19 into a stirring vessel 10, from which the dispersion is recycled through line 20 to the heating or cooling device at a temperature between 60 and 90%. The dispersion is circulated until the contents of the stirring vessel 10 is free of solids and the cleaning liquor has washed substantially all product out of the filter cake. The cleaning liquor may consist of a non-solidifying fluid. For instance, a low-boiling organic solvent with a boiling point of 174° C. may be used, which can be separated from the product by distillation in the separator 16. Alternatively, heated water at 60°–90° C. can be used, which can be separated by a liquid-liquid separation in 16 with low energy consumption.

The mixture of cleaning liquor and a small proportion of the end product is fed to the liquid-liquid separator or distilling device 16. The cleaning liquor which has been removed is recycled to the stirring vessel 10 through line 17. The recovered end product leaves the separator through line 18. A small portion of spent catalyst is withdrawn through line 26 from the filter 7 by cleaning.

During the catalytic hydrogenation, catalyst dispersion is removed at a low rate from the reaction chamber 1 through line 12 and fed to the solid-liquid separator (decanter and/or centrifuge) 11. The separated product is recycled through line 15 to the reaction chamber. A stream containing fine catalyst particles with the size of about 1–10 microns is fed through line 14 to the stirring vessel. Spent catalyst which has been preconcentrated to about 60% can be withdrawn through line 13. The fine catalyst particles are now desirably separated on the filter cake existing in the filter 7 which is due for cleaning.

The embodiment of the process according to the invention shown in FIG. 2 differs from that shown in FIG. 1 in that the existing liquid-liquid separator 21 performs also the function of the separator 16 and the cleaning liquid consists of reaction water 25. The reaction water which has been withdrawn and is mixed with a small amount of product is fed through line 5 to the separator 21 and is mechanically separated therein. Separated end product is transferred through line 27 to the filter 6 and then enters the line 8 for withdrawing the end product. Part of the reaction water withdrawn through line 23 is transferred as cleaning liquor through line 25 to the stirring vessel 10. Another part may be fed through line 22 to the solid-liquid separator 11 as a controlling or rinsing liquid. Product recovered from the stirring vessel 10 is fed through line 24 to the liquid-liquid separator 21 after the catalyst content of the stirring vessel 10 has been entirely removed that the product is circulated through the filter 7 as shown in FIG. 1. The mixture which is delivered from the solid-liquid separator 11 and contains the fine catalyst particles is transferred as in the process according to FIG. 1 through line 14 to the stirring vessel 10 and the fine catalyst particles are separated on the filter cake of the filter which is due for cleaning.

What is claimed is:

1. In a process for the production of a fatty alcohol by catalytic hydrogenation of a feed of fatty acid or fatty acid ester, in a synthesis reactor comprising a high pressure chamber communicating with a return pipe at a temperature of 240° to 330° C. under a pressure of 200 to 700 bar in the presence of a copper chromium oxide containing a catalyst, said catalyst having a particle size of 1 to 500 microns, hydrogen, said feed and said catalyst being fed to said chamber, the contents of said chamber being thoroughly mixed and the hydrogenation being carried out in the presence of material which has already been hydrogenated, surplus hydrogen being withdrawn and recycled to said chamber, the improvement which comprises:

A. withdrawing from said synthesis reactor
   (i) a first product stream containing catalyst,
   (ii) a dispersion containing catalyst and product, and
   (iii) reaction water containing product;

B. treating said first product stream in a first filter and separating product until said first filter, containing a filter cake, is due for cleaning, C. treating said dispersion is a solid-liquid-separator, from said separator withdrawing
   (i) catalyst,
   (ii) a second product stream, and
   (iii) a first mixture, said first mixture containing product and fine catalyst particles with sizes in the range of about 1 to 10 microns, D. recycling said second product stream to the reactor, E. after said first filter is due for cleaning and removing it from service and replacing it with an alternating second filter, treating said first filter, when removed, with a cleaning liquor which is a non-solidifying, organic solvent boiling in the range of 70° to 220° C.;

F. withdrawing a second liquid containing cleaning liquor from said removed first filter, feeding a portion of said second liquor containing cleaning liquor to a stirring vessel and at least a portion of the balance of said second liquor containing cleaning liquor to a distillation zone;

G. from said distillation zone separately withdrawing product and a stream of cleaning liquor, feeding said stream of cleaning liquor into said stirring vessel, also feeding into said stirring vessel said first mixture from said solid-liquid separator;

H. from said stirring vessel, withdrawing a second mixture and while at a temperature of 60° to 90° C. feeding it as said first liquid into said first filter when withdrawn from service, removing catalyst from said removed first filter and alternating said first filter with said second filter whereby to maintain one in filtering position while the other is removed from service and being cleaned.

2. In a process for the production of a fatty alcohol by catalytic hydrogenation of a feed of a fatty acid or fatty acid ester in a synthesis reactor comprising a high pressure chamber communicating with a return pipe at a temperature of 240° to 330° C. under a pressure of 200 to 700 bar in the presence of a copper-chromium oxide containing catalyst, said catalyst having a particle size range of 1 to 500 microns, hydrogen, said feed and said catalyst being fed to said chamber, the contents of said chamber being thoroughly mixed and the hydrogenation being carried out in the presence of material which has already been hydrogenated, surplus hydrogen being withdrawn and recycled to said chamber, the improvement which comprises:

A. withdrawing from said synthesis reactor
   (i) a first product stream containing catalyst,
   (ii) a dispersion containing catalyst and product, and
   (iii) reaction water containing product, B. treating said first product stream in a first filter and separating product until said first filter, containing a filter cake, is due for cleaning, C. treating said dispersion in a solid-liquid-separator, from said separator withdrawing
   (i) catalyst,
   (ii) a second product stream, and
   (iii) a first mixture, said first mixture containing product and fine catalyst particles with sizes in the range of about 1 to 10 microns, D. recycling said second product stream to the reactor, E. said second water containing product from said synthesis reactor being treated in a liquid-liquid-separator, from said liquid-liquid-separator, separately withdrawing a third product stream and an aqueous stream mainly composed of reaction water, introducing at least a portion of said aqueous stream into a stirring vessel;

F. after said filter is due for cleaning, removing it from service and replacing it with an alternating second filter, treating said removed first filter with a first liquid containing reaction water, withdrawing a second liquid from said removed first filter and introducing it into said stirring vessel;

G. feeding said first mixture into said stirring vessel, from said stirring vessel separately withdrawing a fourth product stream and a second mixture, H. feeding at least a portion of said fourth reaction product stream into said liquid-liquid-separator;

I. adjusting the temperature of said second mixture to 60° to 90° C. and feeding it as said first liquid containing reaction water into said removed first filter;

J. removing catalysts from said removed first filter and alternating said first filter with said second filter whereby to maintain one in filtering position while the other is removed from service and being cleaned.

3. A process according to claim 1, wherein said solid-liquid-separator is a decanter or a centrifuge.

4. A process according to claim 1, wherein catalyst withdrawn from said solid-liquid-separator and said removed first filter is dried.

5. A process according to claim 4, wherein said catalyst is dried by passing air therethrough.

6. A process according to claim 2, wherein said solid-liquid-separator is a decanter or a centrifuge.

7. A process according to claim 2, wherein catalyst withdrawn from solid-liquid-separator and said removed first filter is dried.

8. A process according to claim 7, wherein said catalyst is dried by passing air therethrough.

9. A process according to claim 2, wherein said third product stream is introduced into said first filter.

10. A process according to claim 2, wherein said third product stream is mixed with the product separator by said first filter.

* * * * *